United States Patent
Metzinger et al.

(10) Patent No.: US 8,303,600 B2
(45) Date of Patent: Nov. 6, 2012

(54) TARGETING APPARATUS FOR USE IN A MEDICAL PROCEDURE

(75) Inventors: Anthony J. Metzinger, Winona Lake, IN (US); Charles D. Christie, Warsaw, IN (US); Brad A. Parker, Warsaw, IN (US); Andrew H. Berthusen, Warsaw, IN (US)

(73) Assignee: Biomet C.V., Gibraltar (GI)

( * ) Notice: Subject to any disclaimer, the term of this patent is extended or adjusted under 35 U.S.C. 154(b) by 1164 days.

(21) Appl. No.: 12/164,891

(22) Filed: Jun. 30, 2008

(65) Prior Publication Data

US 2009/0326541 A1    Dec. 31, 2009

(51) Int. Cl.
*A61B 17/56*    (2006.01)
(52) U.S. Cl. .............................. 606/98; 606/96; 606/102
(58) Field of Classification Search .............. 606/62–68, 606/96–98, 102, 104
See application file for complete search history.

(56) References Cited

U.S. PATENT DOCUMENTS

| | | | |
|---|---|---|---|
| 5,176,681 A | | 1/1993 | Lawes et al. |
| 5,265,969 A | * | 11/1993 | Chuang ............................ 403/94 |
| 5,334,192 A | | 8/1994 | Behrens |
| 5,474,561 A | * | 12/1995 | Yao ................................. 606/98 |
| 5,562,666 A | | 10/1996 | Brumfield |
| 5,935,127 A | | 8/1999 | Border |
| 6,520,969 B2 | | 2/2003 | Lambrecht et al. |
| 2003/0220651 A1 | * | 11/2003 | Pusnik et al. ................... 606/98 |
| 2005/0203520 A1 | | 9/2005 | Volzow |
| 2006/0224161 A1 | * | 10/2006 | Bhattacharyya .............. 606/102 |
| 2008/0058829 A1 | | 3/2008 | Buscher et al. |

FOREIGN PATENT DOCUMENTS

WO       03041595        5/2003
WO     2006091625        8/2006

OTHER PUBLICATIONS

Strkyer, "Gamma3 tm—The Compact Titanium Version of the Gamma tm Nail System", 2005, US.
International Search Report in corresponding PCT Application (i.e., PCT/US2009/047268), 5 pages.

* cited by examiner

*Primary Examiner* — Thomas Barrett
*Assistant Examiner* — Michael T Schaper
(74) *Attorney, Agent, or Firm* — Harness, Dickey

(57) ABSTRACT

A universal targeting apparatus includes a generally U-shaped body having one end configured to be coupled to the proximal end of the intramedullary implant and a mounting portion at an opposite end of said body. An arm is rotatably mounted to the mounting portion of the U-shaped body and includes bores defined at its opposite ends. Each bore is arranged at a different angle to correspond to the angle of a transverse aperture in the intramedullary implant. The arm can be rotated so an appropriate one of the angled bores is aligned with the transverse aperture to serve as a guide for creating targeting holes in the bone.

14 Claims, 7 Drawing Sheets

TARGETING APPARATUS FOR USE IN A MEDICAL PROCEDURE

BACKGROUND

The present disclosure relates generally to instrumentation used in a medical procedure, and more particularly, relates to a guide or targeting apparatus used in the reduction of a hip fracture.

A procedure regularly performed by orthopaedic surgeons is the reduction of a hip fracture caused by trauma. The site of this type of fracture typically exists at the proximal portion of the femur below the femoral head. In order to reduce a fracture of this type, an elongated lag screw is threadingly advanced into the shaft, neck, and head of the femur. In certain procedures, the proximal end of the lag screw is secured to a bone plate. Cortical screws are used to secure the bone plate to the femur distal to the fracture site. Tightening of the lag screw compresses the bone fragments together and facilitates healing of the femur. Many devices have been designed for this type of reduction including the devices disclosed in U.S. Pat. Nos. 4,438,762, 3,554,193, and 2,526,959, the disclosures of which are incorporated herein by reference in their entirety.

In other procedures, a stabilizing element, such as an intramedullary rod or nail, may be advanced into the medullary canal of the femoral shaft. The intramedullary rod includes a transverse aperture that is oriented at an appropriate angle to support and anchor the proximal portion of the lag screw. In some cases, a compression screw is also introduced into the fractured bone to reduce the fracture. The compression screw also extends through the intramedullary rod adjacent the lag screw. An example of a device of this type is disclosed in U.S. Pat. No. 5,562,666 to Brumfield, the disclosure of which is incorporated herein by reference.

In many surgical procedures, various jigs or similar apparatuses are used to guide the creation of targeting holes in the bone. More specifically, jigs or targeting devices may be used to guide drilling for and insertion of fracture fixation screws, such as the lag and compression screws described above. Proper targeting is more problematic for fixation systems utilizing intramedullary rods/nails, rather than external plates because the transverse openings in the intramedullary implant are contained within the bone and are not directly visible. While various imaging devices may be used to guide a drilling operation or screw insertion, the images are planar and do not easily provide three-dimensional targeting or alignment. Thus, various jigs or targeting devices have been developed to facilitate various steps in the fracture reduction and fixation process.

It is a goal of designers of medical instrumentation to design apparatus used in hip fracture reduction procedures that facilitate implantation of the fracture fixation components in as minimally invasive manner as possible. While many targeting jigs meet this goal, these prior apparatuses are often complex and require assembly of multiple components. Non-modular devices are known that eliminate the plurality of components found in prior modular systems, but at the cost of non-universality—i.e., non-modular devices are designed for only certain specific fixation arrangements, such as a specific angular orientation of a lag screw relative to an intramedullary rod/nail.

What is needed therefore is an assembly used in hip fracture reduction procedures that facilitates implantation a fracture fixation apparatus and simplifies the procedure. The system should be modular and universal without the need for the surgeon to assemble several components before the alignment and targeting steps can be commenced. There is also a need for such an assembly that minimizes or eliminate potential alignment errors that may occur during the procedure.

SUMMARY

To address these needs, a universal targeting apparatus is provided for targeting a transverse aperture in an intramedullary implant, such as a rod or bone nail, for introducing a lag screw into the aperture, in which the transverse aperture has an aperture axis that is oriented at one of at least two angles relative to the longitudinal axis of the intramedullary implant. In one embodiment, the targeting apparatus comprises a generally U-shaped body having one end configured to be coupled to the proximal end of the intramedullary implant and a mounting portion at an opposite end of the body. The mounting portion define a plane with the intramedullary implant when the body is coupled thereto, the plane containing the aperture axis. The apparatus further comprises an arm rotatably mounted to the mounting portion of the U-shaped body that has a first portion and a second portion offset from the first portion. The first portion defines at least one first targeting bore with a longitudinal first axis, while the second portion defines at least one second targeting bore with a longitudinal second axis. In one aspect, the arm is configured so that the first axis is aligned with an aperture axis oriented at one of the at least two angles when the arm is rotated relative to the mounting portion to a first position in which the first axis resides within the plane, and so that the second axis is aligned with an aperture axis oriented at a different one of the at least two angles when the arm is rotated to a different second position in which the second axis resides within the plane.

In certain embodiments, the arm is an elongated bar and the first and second portions are at opposite ends thereof. In one specific embodiment, the arm is mounted to the mounting portion to rotate about an axis in the plane. In another specific embodiment, the arm is mounted to the mounting portion to rotate about an axis perpendicular to the plane. In either embodiment, the targeting arm is configured so that axis of each of the targeting bores will align with the aperture axis of the intramedullary implant when the apparatus is connected to the implant. The apparatus may incorporate a locking mechanism to lock the targeting arm in one of the operative targeting positions so that the corresponding targeting bore may used to create a path in the bone or introduce a lag screw into the implant and bone fracture.

In certain embodiment, the locking mechanism may include a locking magnet mounted to the mounting portion and complementary magnets mounted in each of the first and second portions of the targeting arm. The complementary magnets are configured to be magnetically attracted to the locking magnet to magnetically hold the targeting arm in an operative position. In another embodiment, the locking mechanism includes a depressible pin mounted in one of the arm and the body, and a recess defined in the other of the arm and the body, the recess configured to receive the depressible pin in locking engagement.

In one alternative embodiment, the mounting portion includes two arms spaced apart to define a slot, and the arm is mounted to the mounting portion for rotation within the slot. In this embodiment, the arm is arranged to rotate within the plane defined by the longitudinal axis of the intramedullary implant and the axis of the transverse aperture in the implant.

One benefit of the targeting apparatus disclosed herein is that it is universal in the sense that a single apparatus may accommodate different lag screw angles of an intramedullary implant used for fracture reduction and fixation. Another benefit is that the disclosed apparatus does not require assembly by the surgeon at the surgical site, although the apparatus can accommodate replaceable components to satisfy several lag screw axis angles.

DESCRIPTION OF THE EMBODIMENTS

Figure 1:
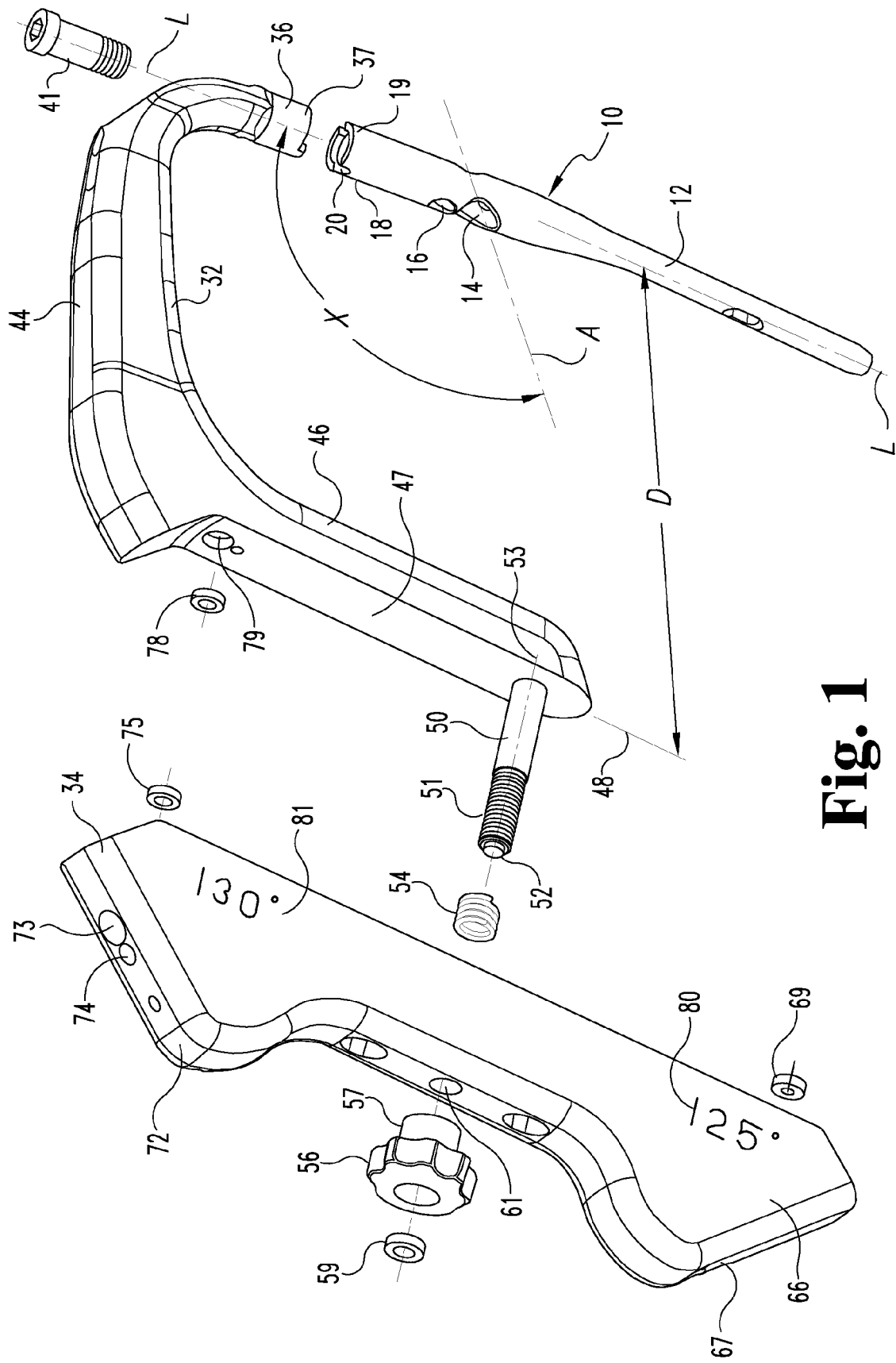
FIG. 1 is an exploded perspective view of one embodiment of a targeting apparatus disclosed herein, along with an intramedullary implant to which the apparatus is mounted.

While the assembly described herein is susceptible to various modifications and alternative forms, specific embodiments thereof have been shown by way of example in the drawings and will herein be described in detail. It should be understood, however, that there is no intent to limit the assembly to the particular forms disclosed, but on the contrary, the intention is to cover all modifications, equivalents, and alternatives falling within the spirit and scope of the invention as defined by the appended claims.

Figure 2:
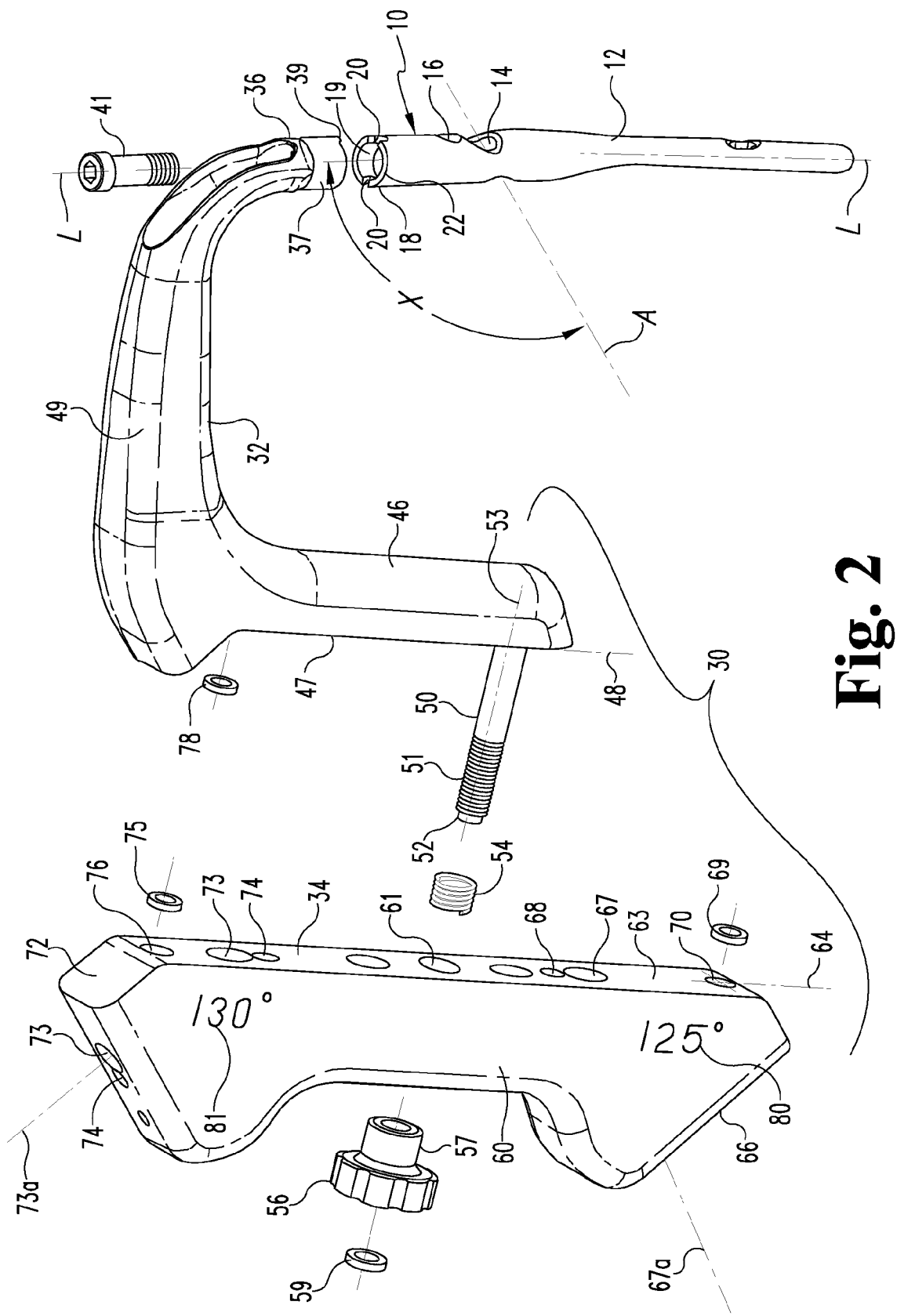
FIG. 2 is an exploded perspective view of the targeting apparatus shown in FIG. 1, with the apparatus viewed from a different angle.
Figure 3:
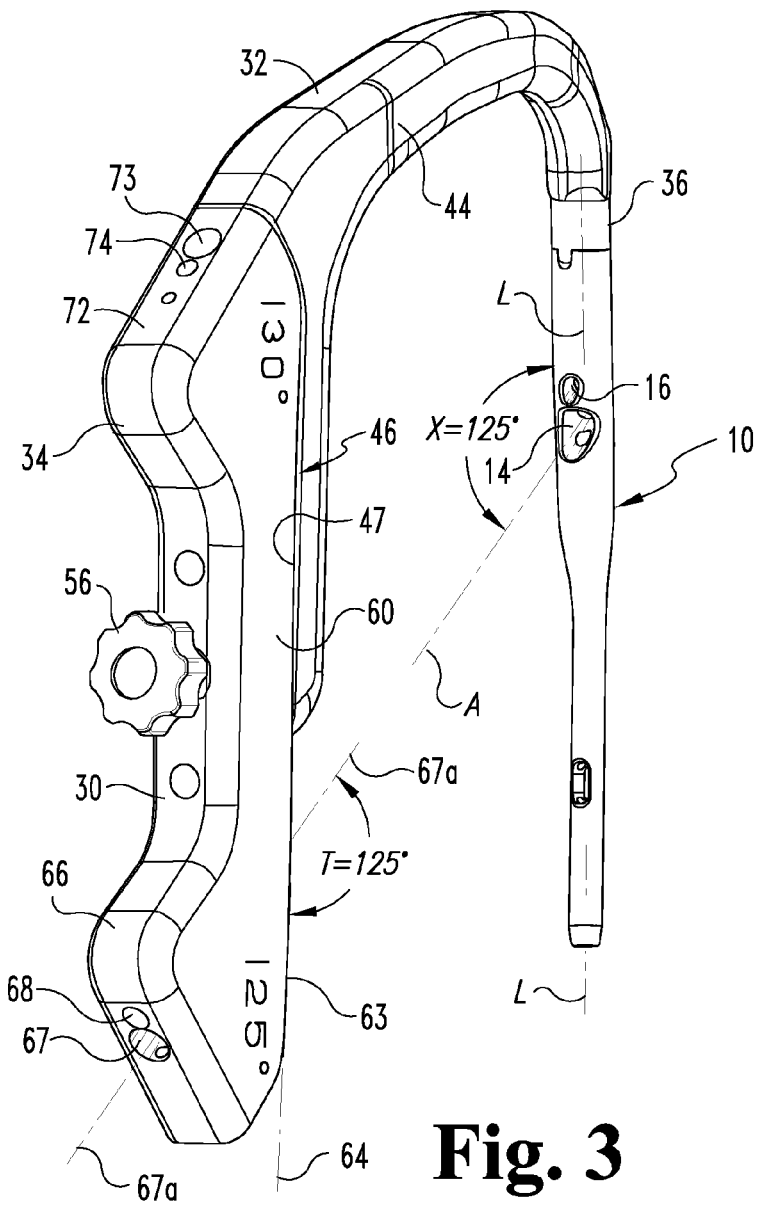
FIG. 3 is a perspective view of the targeting apparatus shown in FIGS. 1-2, with the apparatus assembled and mounted to the intramedullary implant in a first position.

Referring to FIGS. 1-3, a targeting apparatus 30 is shown mounted to an intramedullary implant 10. It is understood that the intramedullary implant 10 would be implanted within the intramedullary canal of the femoral shaft when used in the reduction and fixation of a hip fracture. In accordance with a typical hip fixation procedure, the stem 12 of the intramedullary implant is implanted with the proximal end 18 accessible at the exposed surgical site. The stem 12 is oriented using known techniques so that the transverse apertures 14 and 15 are aligned with the femoral head and the fracture. The transverse aperture 14 is sized to receive a lag screw to reduce and fix the fracture in a known manner. In some procedures, a compression screw may be introduced through the second transverse aperture 15, again in a known manner.

The intramedullary implant 10 preferably defines a bore 19 extending along the longitudinal axis of the stem 12, at least part way along the length of the stem. The bore 19 may define internal threads 22 at the proximal end 18 that are engaged by an insertion tool. The proximal end may also define notches 20 that are also engaged by the insertion tool to facilitate introduction of the intramedullary implant 10 into the femoral shaft.

As shown in FIGS. 1-2, the lag screw transverse aperture 14 is aligned so that the aperture axis A is aligned at a non-perpendicular angle X relative to the longitudinal axis L of the stem 12. This angular orientation corresponds to the non-perpendicular position of the femoral head and neck relative to the femoral shaft. Depending upon the anatomy of the femur and the nature of the fracture, the lag screw may be introduced into the femoral head at different angles. Thus, the angle X of the transverse aperture 14 may be different between different fixation procedures. In the majority of hip procedures, the angle X is either 125° or 130° relative to the longitudinal axis L. In a fewer number of cases other entry angles are indicated.

The targeting apparatus 30 provides a universal apparatus that is capable of targeting drilling and screw insertion for the range of hip procedures. The apparatus 30 includes a generally U-shaped body 32 with a targeting arm 34 pivotably mounted to the body. The body 32 includes a connection end 36 that is configured to be mounted to the proximal end 18 of the intramedullary implant 10. An intermediate portion 44 extends from the connection end 36 to the mounting portion 46, to which the targeting arm 34 is mounted, as described herein.

The configuration of the connection end 36 of the targeting apparatus body is thus dictated by the configuration of the intramedullary implant. For the typical configuration of the intramedullary implant described above, the connection end 36 includes a collar 37 sized to abut the proximal end 18. Prongs 39 extending from the collar are sized to fit within the notches 20 in the end of the member 10. A fastener 41, such as a screw, extends through the collar 37 and into engagement with the internal threads 22 in the bore of the intramedullary implant.

The interaction of the prongs and notches, and the fastener and internal threads, effectively lock the body 32 of the targeting apparatus in a predetermined position relative to the stem 12 and transverse openings 14, 15 of the member 10. More particularly, in this predetermined position the targeting apparatus 30 resides in the plane containing the lag screw transverse aperture 14 and the fractured bone segment to be reduced and fixed. Put another way, the mounting portion 46 includes a mounting axis 48 that falls in the plane defined by the aperture axis A and the longitudinal axis L of the intramedullary implant. Thus, the engagement of the connection end 36 to the proximal end 18 of the member 10 provides the first step in the alignment and targeting function of the apparatus 30.

The intermediate portion 44 of the apparatus 30 forms the base of the general U-shape of the body 32. The portion 44 laterally offsets the mounting portion from the connection end so that the mounting portion 46 is freely accessible outside the patient's limb. The length of the intermediate portion is sized to accommodate the girth of a typical limb. However, the targeting arm must be supported sufficiently close to the intramedullary implant to avoid targeting errors that may be caused by having to traverse the distance D (FIG. 1) between the targeting arm and the transverse aperture 14. For instance, when the targeting arm is used to guide a drill to prepare a bore in the bone to receive a lag screw, the greater the distance D the greater the risk of misalignment of the drill. In certain embodiments, the distance D is in the range of 5-6 inches.

The mounting portion 46 rotatably supports the targeting arm 34 relative to the body 32, and ultimately relative to the intramedullary implant 10 to which the body is connected. The mounting portion defines a mounting surface 47 through which the mounting axis 48 passes. The body 32 is preferably configured so that the mounting surface 47 and axis 48 are parallel to the longitudinal axis L of the member 10 to ensure proper and stable alignment when the targeting procedures are conducted.

In one embodiment, the targeting arm 34 includes an elongated bar 60 that is mounted for rotation about a pivot axis 53 that falls within the plane defined by the longitudinal axis L and aperture axis A so that the bar rotates in a perpendicular plane. Thus, as shown in FIGS. 1-2, the mounting portion 46 includes a pivot post 50 projecting perpendicularly from the mounting surface 47. The post 50 includes a threaded end 51 and terminates in a capture stem 52. The post 50 extends through a pivot bore 61 centrally located in the bar 60. The bar 60 is retained on the pivot post by a knob 56 that includes an internally threaded hub 57 that engages the threaded end 51 of the post. A capture washer 59 may be press fit onto the capture stem 52 to capture the knob 56 on the post 50 and prevent inadvertent disassembly.

In one embodiment, the pivot post 50 is sized so that the targeting arm 34 can freely rotate thereabout and relative to the mounting surface 47. The post 50 is thus sized to permit a gap between the mounting face 63 of the bar 60 and the mounting surface 57 of the body 32. A spring 54 may be concentrically mounted over the pivot post 50 between the face 63 and surface 47 to bias the bar 60 away from the mounting surface. This biased offset thus allows the bar 60 to freely rotate about the post. However, when the bar 60 has been rotated to a desired position, the knob 56 can be manually rotated and threaded down onto the threaded end 51 of the pivot post to reduce the offset or gap between mounting face 63 and mounting surface 47.

In one embodiment, the knob and spring can be configured so that the knob can be tightened until the face 63 abuts the surface 47. It can be appreciated however, that reliance upon a friction engagement between the targeting arm 34 and the mounting portion 46 of the body 32 may not hold the targeting arm in its proper alignment during use. Thus, in another aspect, a locking mechanism is provided that removably locks the targeting arm relative to the mounting portion 46.

In one embodiment the locking mechanism utilizes mutually attracted magnets mounted on the targeting arm and mounting portion. Thus, as shown in FIGS. 1-2, the bar 60 includes a magnet 69 mounted in a recess 70 at a first end 66 of the bar and a magnet 75 mounted in a recess 76 at an opposite second end 72. The mounting portion 46 of the body 32 includes a locking magnet 78 mounted in a recess 79. The three magnets are all mounted at the same radius from the pivot axis 53. Thus, when the second end 72 is arranged as shown in FIGS. 1-2, the two magnets 75 and 78 attract and the magnetic attraction force is sufficiently strong to hold the bar 60 in this position as the targeting apparatus 30 is used in a procedure.

It can be appreciated that when it is desired to rotate the bar 60 so that the first end 66 and its corresponding magnet 69 are aligned with the locking magnet 78, the knob 56 is first unthreaded or loosened along the pivot post 50. As the knob is loosened the biasing spring 54 pushes the bar 60 away from the mounting surface 47. When the knob 56 bottoms against the capture washer 59 the bar is displaced from the mounting portion 46 that the magnetic attraction between the magnets 75 and 78 is sufficiently weak to allow the bar to be easily rotated. Once the bar has been rotated to a position in which the first end 67 is aligned with the locking magnet, the knob 56 can be re-threaded or tightened onto the pivot post 50 until the spring 54 is fully collapsed. In this position, the magnet 69 in the first end 66 is close enough to the locking magnet 78 that the magnetic force can hold or lock the bar 60 in that position for use.

It can be appreciated that the interaction of the magnets 69, 75 relative to the locking magnet 79 not only effective locks the bar 60 in position but also assures an accurate alignment of the targeting arm 34 in its operative positions. In particular, the lines of magnetic force between the opposing magnets 69/75 and 79 are strongest perpendicular to the mounting surface 47 and therefore tend to draw the magnets 69/75 in perpendicular alignment with the locking magnet 79. The bar 60 will hold this aligned position as the knob 56 is tightened.

Maintaining a proper alignment of the bar 60 relative to the mounting portion 46 is important to ensure an accurate alignment of the targeting features of the apparatus 30 relative to the lag screw transverse aperture 14 in the intramedullary implant 10. These targeting features include a first bore 67 defined at the first end 66 of the bar 60 and a second bore 73 at the opposite second end 72. Each bore 67, 73 defines a corresponding bore axis 67a, 73a that forms a non-perpendicular angle relative to the face axis 64 of the mounting face 63 of the bar 60. For instance, as best seen in FIG. 3 the axis 67a of the first bore 67 at the first end of the bar 60 subtends an angle T relative to the mounting axis 48. In the specific example, this angle T is 125° which corresponds to the indicia 80 inscribed on the first end 66 of the bar. It can be readily appreciated that the axis 73a of the second bore 73 in the second end of the bar also subtends an angle with the mounting axis 48, which is 130° in the specific example. Thus, in one feature of this embodiment, the targeting apparatus provides targeting features at two different angles. These two different angles accommodate an intramedullary implant 10 in which the angle X of the aperture axis A is either 125° or 130°. These two angles are most common in implants of this type, but other angles may be accommodated by an appropriately oriented one of the bores 67, 73.

The targeting apparatus 30 is thus configured so that when the bar 60 is locked in one of its two positions the targeting features, namely the appropriate one of the bores 67, 73, is aligned with the transverse aperture 14. As shown in FIG. 3, when the second end 72 is locked by the locking magnet (not shown), the first end is exposed or accessible and the bore axis 67a of the first bore 67 is in direct alignment and collinear with the aperture axis A. Consequently any tool or bone fastener passing through the first bore 67 will be automatically and precisely aligned with the transverse bore 14 in the intramedullary implant 16. In the specific example the first end 66 is in the operable position. If the aperture 14 in the intramedullary implant 10 is aligned at a 130° angle, the bar 60 of the targeting apparatus 30 can be rotated so that the second end 72, bearing the indicia 81 identifying the 130° angle, is in the operative position.

As explained above, in some cases a second screw is introduced through the intramedullary implant in addition to the lag screw. This second screw may be a compression or anti-rotation screw. In those cases, the implant 10 will include a second transverse aperture 16 with its axis parallel to the aperture axis A of the first aperture 16. In some cases this second aperture 16 is independent and offset from the first aperture, while in other cases the two apertures intersect. For implants of this design, the targeting apparatus 30 may incorporate additional bores 68 and 74 in the corresponding first and second ends 66 and 72 of the targeting arm 34, as best seen in FIGS. 1 and 3. The positioning of the added bore 68 relative to the first bore 67, for instance, identically mirrors the positioning of the lag screw bore 14 and compression/anti-rotation screw bore 14 in the implant 10. Accurate positioning of the targeting bores 67, 73 will naturally lead to accurate positioning of the added bores 68, 74.

In the specific embodiment shown in FIGS. 1-3, the most typical lag screw angles are incorporated into the targeting arm. The targeting features, namely the first and second bores 67, 73, respectively, accurate target the lag screw aperture when the bar 60 is locked to the mounting portion 46. When the particular lag screw angle of the intramedullary implant 10 is known, the targeting apparatus 30 can be prepared by rotating the bar 60 so that the appropriate end 66, 72 is in the operative position. Different bars similar to the bar 60 may also be provided in which the targeting bores 67, 73 are aligned at angles other than the 125° and 130° angles shown in the figures. The bar 60 could thus be replaced with the alternative bar by removing the knob 57 and the bar 60 and mounting the alternative bar on the pivot post 50.

Figure 4:
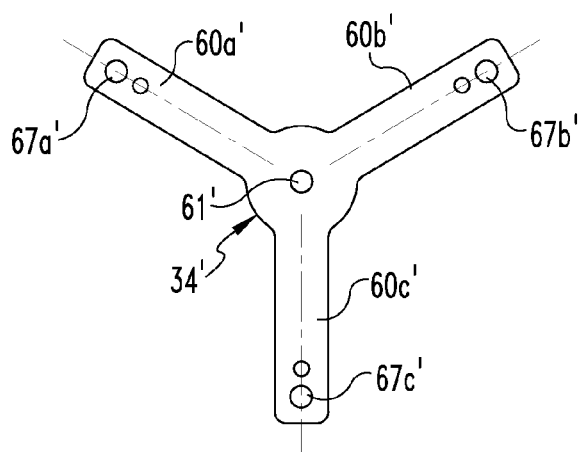
FIG. 4 is a top view of a targeting arm of an alternative design for use in the apparatus shown in FIG. 1-3.

One alternative targeting arm 34' is shown in FIG. 4. This targeting arm 34' includes three bar segments 60a', 60b' and 60c', each defining a corresponding targeting bore 67a', 67b' and 67c'. The segments are evenly distributed around and radiate from a central pivot bore 61' that is configured to rotatably mount the targeting arm 34' on the pivot post 50 (FIG. 1). Each of the targeting bores 67a', 67b' and 67c' is aligned at a different angle to correspond to one of three lag screw angles for the intramedullary implant 10. With this particular embodiment, the magnetic locking mechanism described above may be used with some modification. Specifically, since the bar segments 60a', 60b' and 60c' are spaced at 120° intervals, it is not possible to provide a magnet 180° a particular bar segment that can engage the locking magnet 78 situated in the mounting portion 46. In one modification, the magnet corresponding to each segment may be positioned immediately adjacent the pivot bore 61 in alignment with the corresponding segment. The locking magnet 78 would also be relocated to a position adjacent the pivot post 50.

Figure 5:
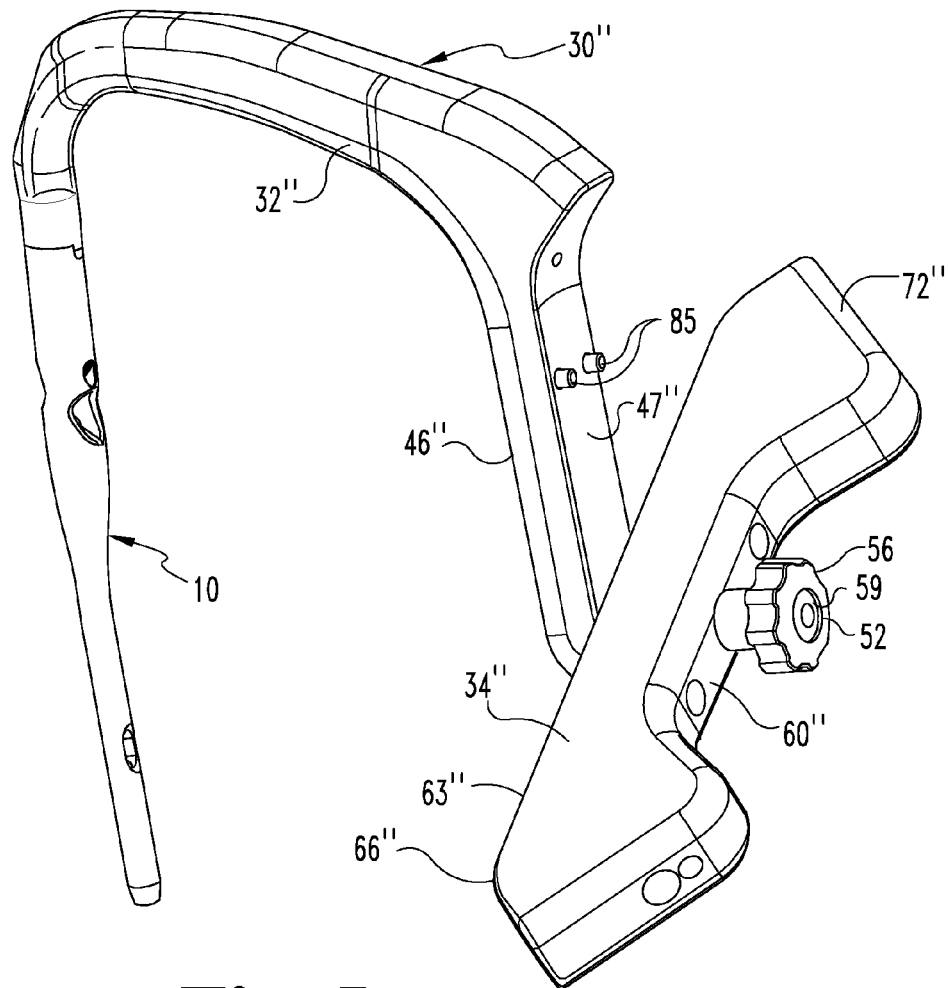
FIG. 5 is a perspective view of a modified targeting apparatus shown with the apparatus in a rotated second position.
Figure 6:
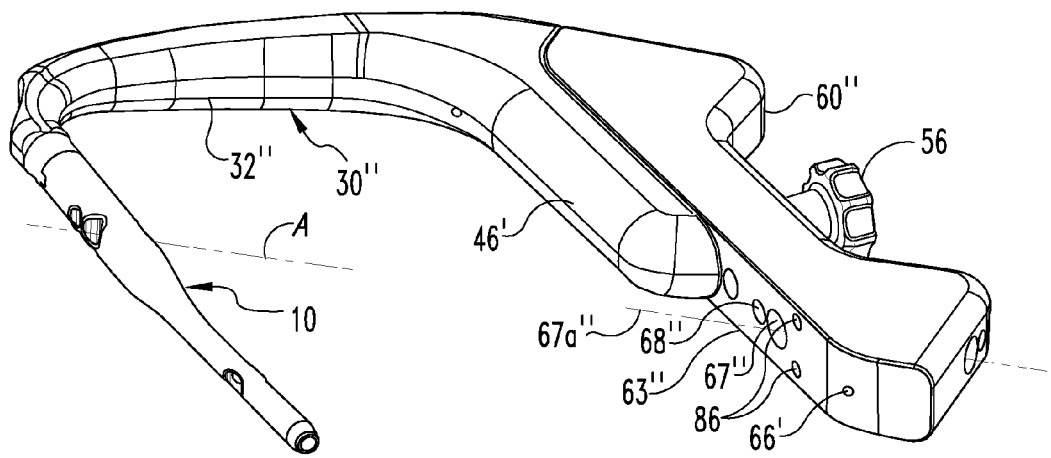
FIG. 6 is a perspective view of the targeting apparatus shown in FIG. 5 with the apparatus in a different third position.

As shown in FIGS. 5-6, an alternative non-magnetic locking mechanism may be provided to lock the targeting arm in position. In this embodiment, a pair of locking pins 85 project from the mounting surface 47" of the mounting portion 46". The mounting face 63" of the targeting arm 34" is modified form the prior embodiment to include two locking recesses 86. The recesses 86 are positioned to receive the corresponding locking pins 85 when the bar 60" is aligned with the mounting portion 46", as illustrated in FIG. 6. The interface between the pins 85 and recesses 86 is configured to allow rotation of the bar to and from the operable positions, while positively locking the bar in those operable positions. In one embodiment, the pins are rigidly fixed to the mounting portion so that the knob must be untightened and the bar 60 elevated sufficiently above the mounting surface 47" to clear the locking pins during rotation. In another specific embodiment, the locking pins 85 are depressible so that the pins are depressed as the bar 60" is rotated into one of the two operative positions. The pins may be spring mounted within the mounting portion 46" or may be formed of a resiliently depressible material.

Figure 7:
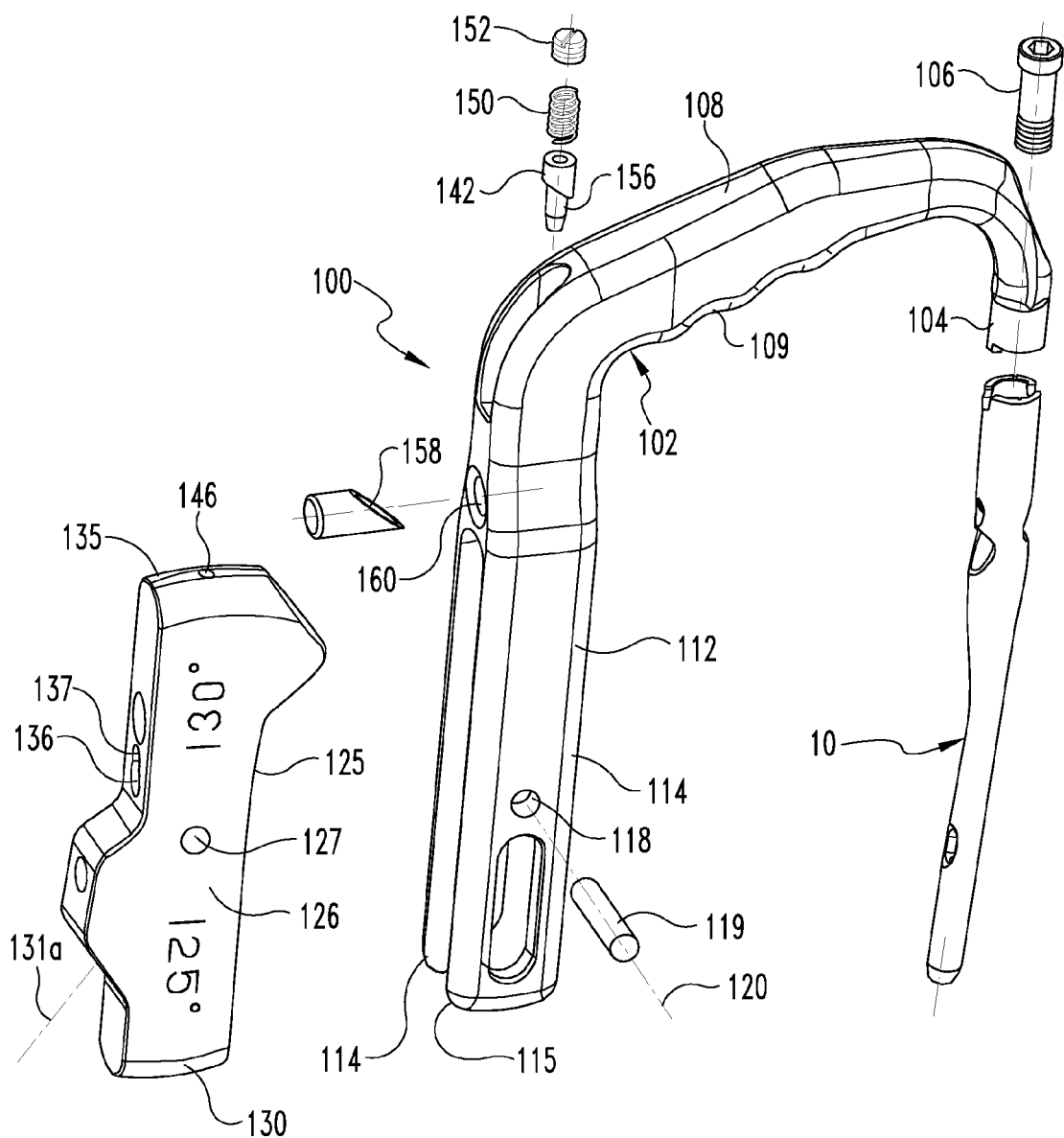
FIG. 7 is an exploded perspective view of a targeting apparatus according to a further embodiment disclosed herein.
Figure 8:
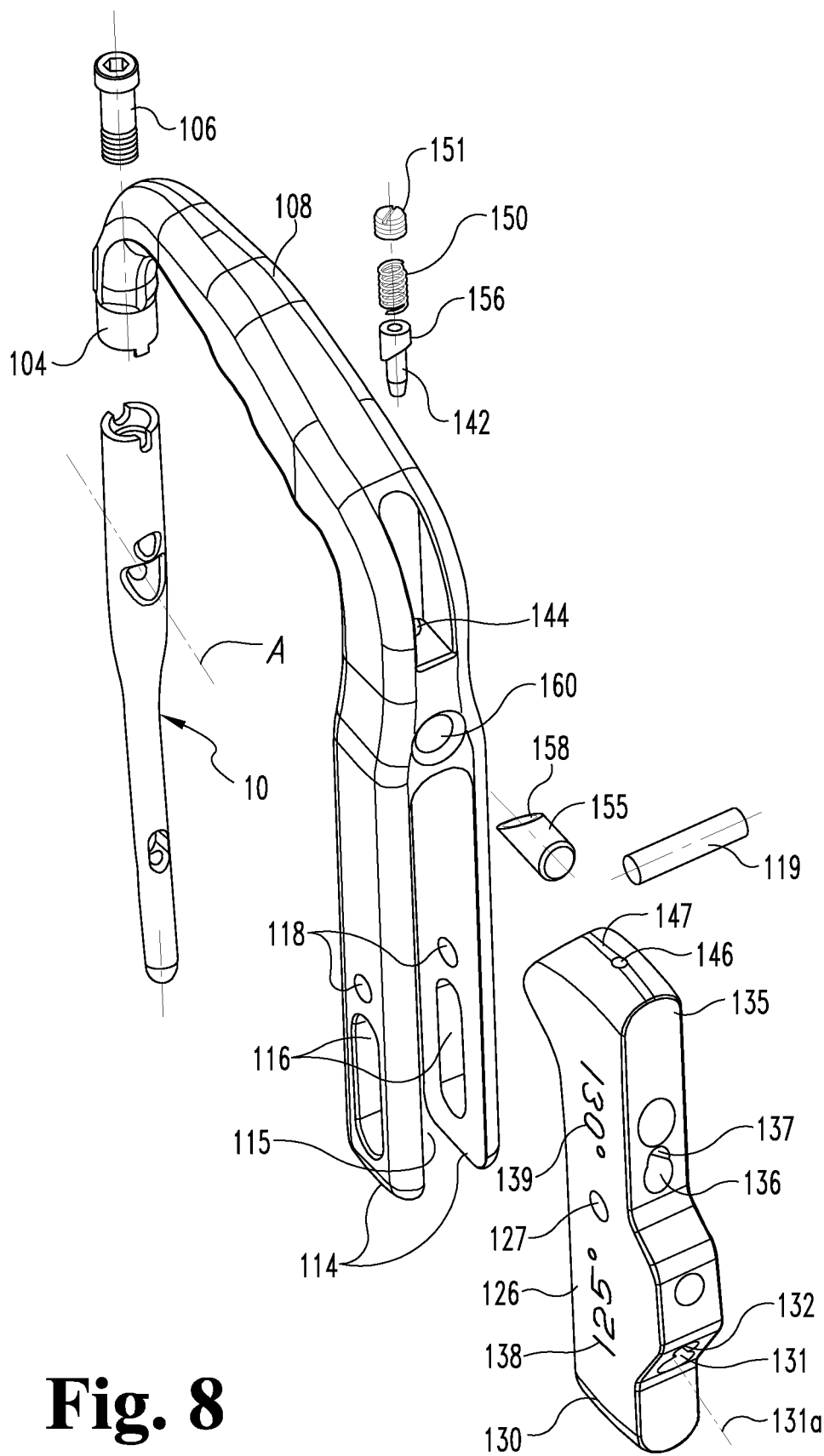
FIG. 8 is an exploded perspective view of the targeting apparatus shown in FIG. 7, as viewed from a different angle.

In an alternative embodiment illustrated in FIGS. 7-9, a targeting apparatus 100 includes a targeting arm 125 that is rotatable in the plane common to the aperture axis A and longitudinal axis L of the intramedullary implant 10. Thu, the targeting apparatus 100 includes a generally U-shaped body 102 having a mounting end 104 and fastener 106 that are configured to mate with features in the proximal end of the implant, as described above. The intermediate portion 108 of the body 102 may define a hand grip feature 109.

In a modification from the apparatus 30 of the prior embodiment, the apparatus 100 includes a mounting portion 112 that is formed by two arms 114 that are spaced apart to define a slot 115 therebetween. The arms are configured so that the slot 115 extends parallel to the plane defined by the two implant axes A and L. The arms 115 further define aligned bores 118 for receiving a pivot pin 119, preferably in a press-fit or friction-fit arrangement. The pivot pin 119 defines a pivot axis 120 about which the targeting arm 125 rotates that is perpendicular to the plane of axes A and L.

The apparatus 100 further includes a targeting arm 125 in the form of a bar 126 supported by the pin 119 extending through a pivot bore 127. The first end 130 of the bar 126 defines a first bore 131 along a bore axis 131a, as well as an additional bore 132 where necessary. Likewise, the opposite second end 135 defines a second bore 136 and additional bore 137. As with the prior embodiment, the two ends may include corresponding indicia 138, 139 identifying the particular angular orientations of the targeting bores 131, 136. The arms 114 of the mounting portion 112 may further define windows 116 to permit direct visualization of the indicia when the targeting arm is in an operative position.

As with the prior embodiment, a locking mechanism may be provided to positively lock the targeting arm in one of its operative positions. The locking mechanism may include a locking pin 42 that extends through a bore 144 in communication with the slot 115. The end of the locking pin 142 is configured to reside within a dimple 146 defined in each end 130, 135 of the bar 126. The depth of engagement of the tip of the locking pin within the dimple 146 is sufficient to restrain or lock the targeting arm in its operative targeting positions.

The locking pin 142 in one embodiment is retractable from the dimple 146 to allow the bar to freely rotate within the slot 115. Thus, a biasing spring 150 may be captured behind the locking pin 142 by a set screw 152 threaded engaged within bore 144. The spring 150 thus biases the locking pin into engagement with the locking dimples in the targeting arm bar 126. A manually depressible release button 155 is disposed within a cross bore 160 in the mounting portion 112 to intersect the locking pin bore 144. The locking pin and release button define complementary mating angled surfaces 156, 158, respectively. The angled surfaces 156, 158 are configured and arranged so that when the button 155 is depressed, the interaction between the angled surfaces tends to push the locking pin 142 back against the biasing spring 150 and away from the locking dimple 146.

As long as the button is depressed, the mating angled surfaces 156, 158 hold the locking pin disengaged from the locking dimple so that the bar 126 can freely rotate within the slot 115. When the button 155 is released, the biasing spring 150 pushes the locking pin back toward the targeting arm bar 126 and pushes the button back along the cross bore 160. In a specific embodiment, the ends 130, 135 of the bar 126 define arcuate grooves 147 that intersect a corresponding locking dimple 146. These arcuate grooves accept the locking pin while it is extended into the slot 115 as the bar 126 is rotated and guide the locking pin toward the deeper locking dimple 146. The biasing spring 150 will then propel the locking pin into the dimple 146 to hold the bar in the operative targeting position.

Figure 9C:
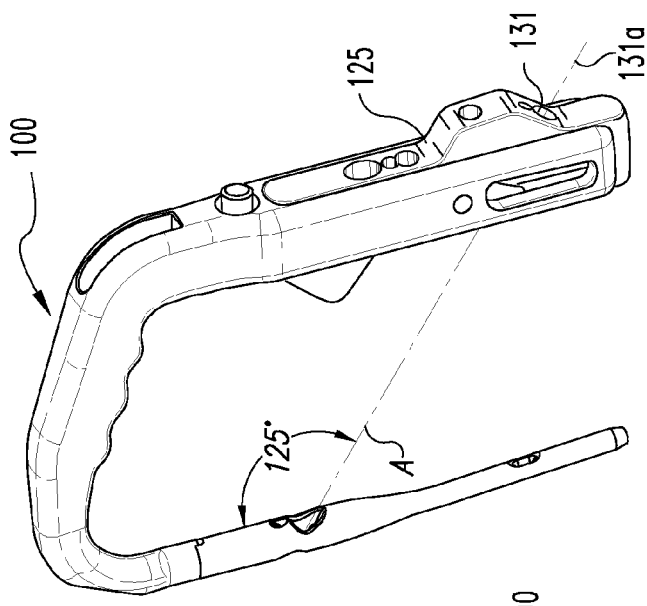
FIGS. 9a-c are perspective views of the targeting apparatus shown in FIGS. 7-8, with the apparatus depicted in sequential positions.
Figure 9B:
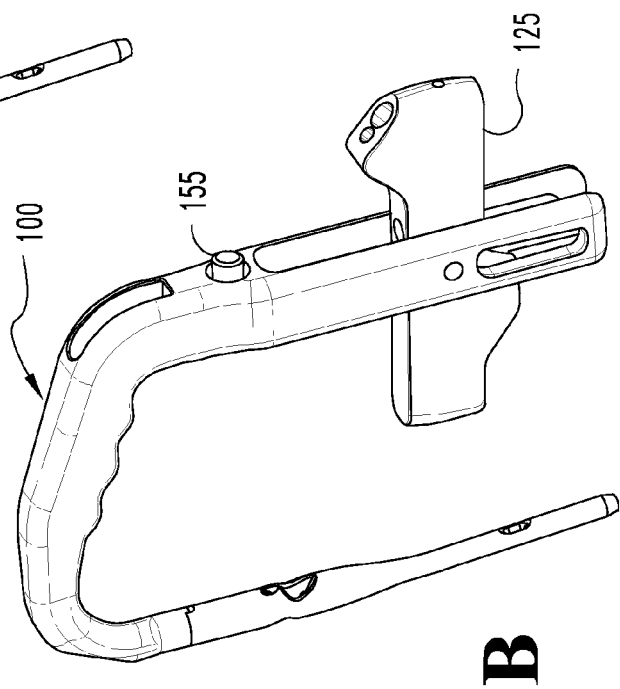
Figure 9A:
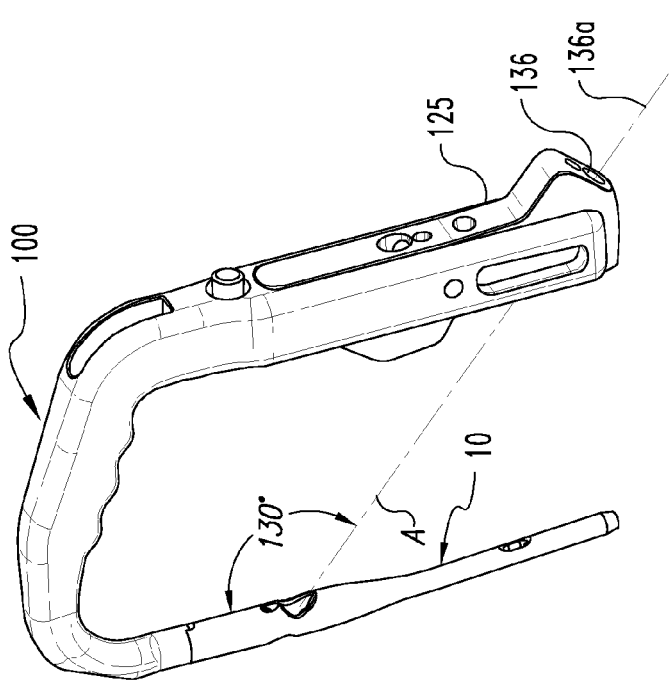

The different positions of the targeting arm 125 are illustrated in the sequence shown in FIGS. 9a-9c. In the first position, the second bore 136 is oriented with the targeting bore axis 136a aligned with the aperture axis A at an angle of 130°, as shown in FIG. 9a. The button 155 is depressed to retract the locking mechanism and release the targeting arm 125 to rotate, as shown in FIG. 9b. The targeting arm continues to rotate until the arm is locked in the position shown in FIG. 9c in which the axis 131a of the first targeting bore 131 is aligned with the axis A at an angle of 125°.

There are many advantages arising from the various features of each of the embodiments of the assembly described herein. It will be noted that alternative embodiments of the assembly may not include all of the features described yet still benefit from at least some of the advantages of such features. Those of ordinary skill in the art may readily devise their own implementations of the assembly that incorporates one or more of the features and fall within the spirit and scope of the present invention as defined by the appended claims.

What is claimed is:

1. A universal targeting apparatus for targeting a transverse aperture in an intramedullary implant, being one of a rod or bone nail, for introducing a lag screw into the aperture, in which the transverse aperture has an aperture axis that is oriented at one of at least two angles relative to a longitudinal axis of the intramedullary implant, comprising:
a generally U-shaped body having one end configured to be coupled to the proximal end of the intramedullary implant and a mounting portion at an opposite end of said body, said mounting portion defining a mounting portion longitudinal axis and a plane with the intramedullary implant when the body is coupled thereto, said plane containing the aperture axis; and
an arm rotatably mounted to said mounting portion of said U-shaped body and having a first portion and a second portion offset from said first portion, said first portion defining a first portion longitudinal axis and at least one first bore with a longitudinal first axis, and said second portion defining a second portion longitudinal axis and at least one second bore with a longitudinal second axis, said arm configured so that said longitudinal first axis is aligned with an aperture axis oriented at one of the at least two angles when said arm is rotated relative to said mounting portion to a first position in which said longitudinal first axis resides within said plane, and so that said longitudinal second axis is aligned with an aperture axis oriented at a different one of the at least two angles when said arm is rotated to a second position, different than said first position, in which said longitudinal second axis resides within said plane, wherein one of said first portion and said second portion longitudinal axes is substantially aligned with said mounting portion longitudinal axis when said arm is in one of said first position and said second position and said first portion and second portion longitudinal axes are misaligned with said mounting portion longitudinal axis when said arm is not in either of said first position or said second position, wherein said arm is mounted to said mounting portion to rotate about an axis in said plane.

2. The universal targeting apparatus of claim 1, wherein said arm is an elongated bar and said first and second portions are at opposite ends thereof.

3. The universal targeting apparatus of claim 1, wherein said body is configured so that said mounting portion is parallel to the longitudinal axis of the intramedullary implant when the body is coupled thereto.

4. The universal targeting apparatus of claim 3, wherein:
said arm is an elongated bar and said first and second portions are at opposite ends thereof; and
said arm is mounted on said mounting portion so that said bar remains parallel to said mounting portion as said arm rotates relative thereto.

5. The universal targeting apparatus of claim 1, in which the transverse aperture has an aperture axis that is oriented at one of three different angles relative to the longitudinal axis, the orientation of each of the three different angles defining three different aperture axes, wherein:
said arm includes a third portion offset from said first and second portions, said third portion defining at least one third bore with a longitudinal third axis; and
said arm is configured so that said longitudinal first axis is aligned with a first one of the three different aperture axes in said first position, said longitudinal second axis is aligned with a second one of the three different aperture axes in said second position, and said longitudinal third axis is aligned with a third one of the three different aperture axes when said arm is rotated relative to said mounting portion to a third position in which said longitudinal third axis resides within said plane.

6. The universal targeting apparatus of claim 1, further comprising a locking mechanism between said body and said arm to lock said arm in at least one of said first position and said second position.

7. The universal targeting apparatus of claim 6, wherein said locking mechanism includes a locking magnet mounted to said mounting portion and each of said first and second portions include a corresponding complementary magnet mounted thereto, each complementary magnet configured to be magnetically attracted to said locking magnet.

8. The universal targeting apparatus of claim 6, wherein said locking mechanism includes a depressible pin mounted in one of said arm and said body, and a recess defined in the other of said arm and said body, said recess configured to receive said depressible pin in locking engagement.

9. The universal targeting apparatus of claim 8, wherein said depressible pin is mounted in said body and each of said first portion and second portion of said arm defines a recess configured to receive said depressible pin.

10. The universal targeting apparatus of claim 8, wherein said depressible pin includes a spring arranged to resist depressing said pin.

11. The universal targeting apparatus of claim 10, wherein said locking mechanism includes a manually pressed button arranged to depress said pin against said spring.

12. The universal targeting apparatus of claim 1, in which the proximal end of the intramedullary implant includes at least two notches offset from each other, wherein said one end of said body defines at least two prongs configured and arranged to engage a corresponding one of the notches.

13. The universal targeting apparatus of claim 1, wherein each of said first portion and second portion includes an indicia indicative of the corresponding one of the aperture axis angles.

14. The universal targeting apparatus of claim 1, in which the intramedullary implant includes an additional transverse aperture for receiving a compression member, wherein each of said first and second portions defines an additional bore aligned with the corresponding first and second bore.

* * * * *

UNITED STATES PATENT AND TRADEMARK OFFICE
CERTIFICATE OF CORRECTION

PATENT NO. : 8,303,600 B2
APPLICATION NO. : 12/164891
DATED : November 6, 2012
INVENTOR(S) : Anthony J. Metzinger et al.

It is certified that error appears in the above-identified patent and that said Letters Patent is hereby corrected as shown below:

Column 1,
Line 64, after "implantation" insert --of--

Column 2,
Line 2, replace "eliminate" with --eliminates--

Column 2,
Line 17, replace "define" with --defines--

Column 2,
Line 46, after "may" insert --be--

Column 2,
Line 48, replace "embodiment" with --embodiments--

Column 3,
Line 19, replace "FIG. 1-3" with --FIGS. 1-3--

Column 6,
Line 2, replace "effective" with --effectively--

Column 6,
Line 6, replace "69/75" with --69, 75--

Column 6,
Line 7, replace "69/75" with --69, 75--

Column 7,
Line 4, replace "accurate" with --accurately--

Signed and Sealed this
Nineteenth Day of February, 2013

Teresa Stanek Rea
*Acting Director of the United States Patent and Trademark Office*

Column 7,
Line 39, replace "form" with --from--

Column 7,
Line 58, replace "Thu," with --Thus,--

Column 8,
Line 32, replace "threaded," with --threadably--